(12) United States Patent
Hummersone et al.

(10) Patent No.: US 7,642,254 B2
(45) Date of Patent: *Jan. 5, 2010

(54) ATM INHIBITORS

(75) Inventors: Marc Geoffrey Hummersone, Horsham (GB); Keith Allan Menear, Horsham (GB); Laurent Jean Martin Rigoreau, London (GB); Graeme Cameron Murray Smith, Cambridge (GB); Niall Morrison Barr Martin, Cambridge (GB); Roger John Griffin, Morpeth (GB)

(73) Assignee: Kudos Pharmaceuticals Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/351,052

(22) Filed: Feb. 9, 2006

(65) Prior Publication Data

US 2006/0178361 A1 Aug. 10, 2006

Related U.S. Application Data

(60) Provisional application No. 60/651,174, filed on Feb. 9, 2005.

(51) Int. Cl.
*A61K 31/535* (2006.01)
*A61K 31/38* (2006.01)
*A61K 31/35* (2006.01)
*C07D 413/14* (2006.01)
*C07D 409/14* (2006.01)
*C07D 407/14* (2006.01)

(52) U.S. Cl. ............... 514/232.8; 514/437; 514/460; 544/145; 549/26; 549/415

(58) Field of Classification Search ............ 549/26, 549/415; 514/232.8, 437, 460; 544/145
See application file for complete search history.

(56) References Cited

U.S. PATENT DOCUMENTS

| | | | |
|---|---|---|---|
| 4,954,518 A | 9/1990 | Takano et al. | |
| 5,252,735 A | 10/1993 | Morris | |
| 5,284,856 A | 2/1994 | Naik et al. | |
| 5,302,613 A | 4/1994 | Morris | |
| 5,703,075 A | 12/1997 | Gammill et al. | |
| 5,733,920 A | 3/1998 | Mansuri et al. | |
| 5,922,755 A | 7/1999 | Tanaka et al. | |
| 6,348,311 B1 | 2/2002 | Kastan et al. | |
| 6,387,640 B1 | 5/2002 | Kastan et al. | |
| 7,049,313 B2* | 5/2006 | Smith et al. | 514/231.5 |
| 7,056,942 B2* | 6/2006 | Hildesheim et al. | 514/411 |
| 2004/0002492 A1* | 1/2004 | Murray Smith et al. | 514/225.2 |
| 2004/0023968 A1 | 2/2004 | Martin et al. | |
| 2004/0192687 A1 | 9/2004 | Martin et al. | |
| 2005/0054657 A1 | 3/2005 | Smith et al. | |
| 2005/0107367 A1 | 5/2005 | Martin et al. | |
| 2006/0106025 A1 | 5/2006 | Smith et al. | |
| 2006/0264427 A1 | 11/2006 | Smith et al. | |
| 2006/0264623 A1 | 11/2006 | Smith et al. | |
| 2007/0238729 A1 | 10/2007 | Martin et al. | |
| 2007/0238731 A1 | 10/2007 | Smith et al. | |
| 2008/0242664 A1 | 10/2008 | Smith et al. | |
| 2009/0042865 A1 | 2/2009 | Frigerio | |
| 2009/0043091 A1 | 2/2009 | Smith et al. | |

FOREIGN PATENT DOCUMENTS

| | | |
|---|---|---|
| EP | 0 610 519 A1 | 8/1994 |
| EP | 0 635 268 A1 | 1/1995 |
| EP | 0 640 339 A1 | 3/1995 |
| EP | 0 641 566 A1 | 3/1995 |
| EP | 0 648 492 A2 | 4/1995 |
| EP | 0 658 343 A1 | 6/1995 |
| GB | 1303724 | 1/1973 |
| GB | 2 302 021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |
| WO | WO 95/29673 | 11/1995 |

(Continued)

OTHER PUBLICATIONS

Abraham, Robert T., "Cell cycle checkpoint signaling through the ATM and ATR kinases," *Genes & Dev.*, 15: 2177-2196 (2001).

(Continued)

*Primary Examiner*—Rebecca L Anderson
*Assistant Examiner*—Joseph R Kosack
(74) *Attorney, Agent, or Firm*—Michael Best & Friedrich LLP

(57) ABSTRACT

A compound of formula I:

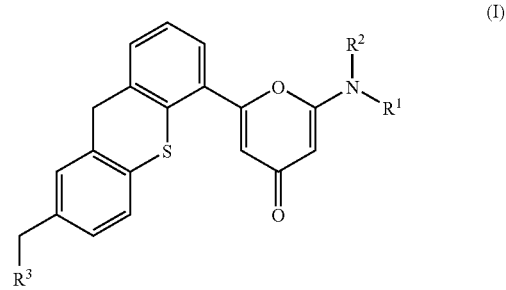

(I)

and isomers, salts, solvates, chemically protected forms, and prodrugs thereof, wherein:

$R^1$ and $R^2$ together form, along with the nitrogen atom to which they are attached, an optionally substituted nitrogen containing heterocyclic ring having from 4 to 8 ring atoms; and $R^3$ is selected from hydroxy and —$NR^{N1}R^{N2}$, where $R^{N1}$ and $R^{N2}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted nitrogen containing heterocyclic ring having from 4 to 8 ring atoms, and its use in inhibiting ATM.

3 Claims, No Drawings

FOREIGN PATENT DOCUMENTS

| | | |
|---|---|---|
| WO | WO 96/01108 | 1/1996 |
| WO | WO 97/15658 | 5/1997 |
| WO | WO 97/18323 | 5/1997 |
| WO | WO 98/55602 | 12/1998 |
| WO | WO 98/56391 | 12/1998 |
| WO | WO 99/47494 | 9/1999 |
| WO | WO 01/53266 A1 | 7/2001 |
| WO | WO 02/20500 A2 | 3/2002 |
| WO | WO 02/056912 A2 | 7/2002 |
| WO | WO 03/024949 A1 | 3/2003 |
| WO | WO 03/034997 A2 | 5/2003 |
| WO | WO 03/035618 A2 | 5/2003 |
| WO | WO 03/070726 | 8/2003 |
| WO | WO 03/093261 | 11/2003 |
| WO | 2006032869 | 3/2006 |

OTHER PUBLICATIONS

Archer, S. et al., "Ring-Hydroxylated Analogues of Lucanthone as Antitumore Agents," *J. Med Chem.*, 25, 220-227 (1982).
Banin, S., et al., "Enhanced phosphorylation of p53 by ATM in response to DNA damage," *Science*, 281:1674-1677 (1998).
Bantick, J.R., et al., "Synthesis of 2-aminochromones," *J. Heterocyclic Chem.*, 1981, vol. 18, pp. 679-684.
Berge, Stephen M., et al., "Review article," *J. Pharm. Sci.*, 66:1, pp. 1-19 (1977).
Bettoni, et al., "Synthesis and absolute configuration of substituted morpholines," *Tetrahedron*, 1980, vol. 36, pp. 409-415.
Boyd, J., et al., "The chemistry of the 'insoluble red' woods," *J. Chem. Soc.*, 1948, pp. 174-176.
Brown, P.O., "Integration of retroviral DNA," *Curr Top Microbiol Immunol.*, 157:19-48 (1990).
Buon, C., et al., "Synthesis of 3-substituted and 2,3-disubstituted-4H-1,4- Benzoxazines," *Tetrahedron*, 2000, vol. 56, pp. 604-614.
Chiosis, G, et al. "LY294002-geldanamycin heterodiamers as selective inhibitors of the P13K and P13k-related family", *Bioorganic & Medicinal Chemistry Letters*, vol. 11, No. 7, Apr. 9, 2001 pp. 909-913, XP004232522.
Daniel, R., et al., "A role for DNA-PK in retroviral DNA integration," *Science*, 1999, vol. 284, pp. 644-647.
Daniel, Rene, et al., "Wortmannin potentiates integrase-mediated killing of lymphocytes and reduces the efficiency of stable transduction by retroviruses," *Mol. Cell Biol*, 21:4, 1164-1172 (2001).
Datta, A., et al., "Reformatsky reaction on aroylketene S, N-acetals: a facile route to 4-amino-6-aryl-2H-pyran-2-ones," *Synthesis*, 1988, vol. 3, pp. 248-250.
DI Braccio, M., et al., "1,2-fused pyrimidines VII," *Eur. J. Med., Chem.*, 1995, vol. 30, No. 1, pp. 27-38.
DI Braccio, M., et al., "Pyran derivatives XIX. (Dialkylamino) substituted 1-benzopyranones and naphthopyranoes with platelet antiaggregating activity," *Farmaco*, 1995, vol. 50, No. 10, pp. 703-711.
Durocher, Daniel, and Jackson, Stephen P., "DNA-PK, ATM and ATR as sensors of DNA damage: variations on a theme?," *Curr Opin Cell Biol.*, 13:225-231 (2001).
Ermili, A., et al., "Chemical and pharmacological research on pyran derivatives," Enclosed: *Chemical Abstracts*, 1977, vol. 87, No. 15, p. 588 (XP-002218602), 117750g.
Gell, D., et al., "Mapping of protein-protein interactions within the DNA-dependent protein kinase complex," *Nucleic Acid Res.*, 1999, vol. 27, No. 17, pp. 3494-3502.
Giroux, A., et al, "One pot biaryl synthesis via in situ boronate formation," *Tet. Lett.*, 38:22, 3841-3844 (1997).
Goytisolo, et al., "The absence of DNA-dependent protein kinase catalytic subunit in mice results in anaphase bridges and in increased telomeric fusions with normal telomere length and G-strand overhang," *Mol. Cell. Biol.*, 2001, vol. 21, No. 11, pp. 3642-3651.
Green, T. and Wuts, P., ed., *Protective Groups in Organic Synthesis*, Wiley (1999).
Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Humn Tumor Cell Line in Vitro", *J. Med. Chem.*, 2005, 48, 569-585.
Hartley, K. O., et al., "DNA-dependent protein kinase catalytic subunit: a relative of phosphatidylinositol 3-kinase and the ataxia telengiectasia gene product," *Cell*, 1995, vol. 82, pp. 849-856.
Haselhorst, Dorte, et al., "Development of cell lines stably expressing human immunodeficiency virus type 1 proteins for studies in encapsidation and gene transfer," *J Gen Virol*, 79: 231-237 (1998).
Herzog, Karl-Heinz et al., "Requirement for ATM in ionizing radiation-induced cell death in the developing central nervous system," *Science*, 280: 1089-1091 (1998).
Hickson, Ian, et al, "Identification and Characterization of a Novel and Specific Inhibitor of the Ataxia-Telangiectasia Mutated Kinase ATM," *Cancer Research* 64, Dec. 15, 2004, 9152-9159.
Hollick, J J, et al., "2,6-Disubstituted pyran-4-one and thiopyran-4-one inhibitors of DNA-dependent protein kinase" *Bioorganic and Medicinal Chemistry Letters*, vol. 13, No. 18, Sep. 15, 2003 pp. 3083-3086, XP002303369.
Ishiyama, T. et al., "Synthesis of arylboronates via the palladium(0)-catalyzed cross-coupling reaction of tetra(alkoxo)diborons with aryl triflates," *Tett. Lett.*, 38:19, 3447-3450 (1997).
Ismail, I.H. et al., Oncogene (2004) 23:873-883.
Izzard, R.A., et al., "Competitive & noncompetitive inhibition of the DNA-dependent protein kinase," *Cancer Research*, 1999, vol. 59, No. 11, pp. 2581-2586.
Jackson, S. P., "DNA damage detection by DNA dependent protein kinase and related enzymes," *Cancer Surv.*, 1996, vol. 28, pp. 261-279.
Jung, J. C., et al., "Simple and cost effective synthesis of 4-hydroxycoumarin," *Synth. Commun.*, 1999, vol. 29, No. 20, pp. 3587-3595.
Kashishian, A. et al., Mol. Cancer Ther. (2003) 2:1257-1264.
Keith, Curtis T. and Schreiber, Stuart L., "PIK-related kinases: DNA repair, recombination, and cell cycle checkpoints," *Science*, 270: 50-51 (1995).
Knight, A.R., et al., "Isolation and characterization of 4-chloro-3,4'; 3',4"-tercoumarin," *Can. J. Chem.*, 1968, vol. 46, pp. 2495-2499.
Kubik, et al., "Fine tuning of the cation affinity of artificial receptors based on cyclic peptides by intramolecular conformational control," *Eur. J. Org. Chem.*, 2001, pp. 311-312.
Lau et al., Nature Cell Biology (2005) 7:493-500.
Lavin, Martin F. and Shiloh, Yosef, "The genetic defect in ataxia-telangiectasia," *Annu. Rev. Immunol*, 15:177-202 (1997).
Leahy, et al., "Identification of a highly potent and selective DNA-dependent protein kinase (DNA-PK) inhibitor (NU7441) by screening of chromenone librariest", *Bioorganic & Medicinal Chemistry Letters* 14 (2004) 6083-6087.
Metcalfe, Judith A. et al., "Accelerated telomere shortening in ataxia telangiectasia," *Nature Genetics*, 13: 350-353 (1996).
Mlotkowska, B.L. et al., "Two-dimensional NMR studies of 2-substituted thioxanthene sulfoxides," *J. Heterocyclic Chem.*, 28: 731-736 (Apr.-May 1991).
Morris, J., et al., "Synthesis and biological evaluation of antiplatelet 2-aminochromones," *J. Med. Chem.*, 1993, vol. 36, No. 14, pp. 2026-2032.
Morris, J., et al., "Synthesis of 2-amino-6-phenyl-4H-pyran-4-ones," *Synthesis*, 1994, pp. 43-46.
Morris, J., et al., "Reaction of phosgeniminium salts with enolates derived from Lewis acid complexes of 2'-hydroxypropiophenones and related β-Diketones," *J. Org. Chem.*, 1996, vol. 61, No. 9, pp. 3218-3220.
Muller, C. et al., Blood (1998) 92:2213-2219.
Naldini, Luigi et al., "In vivo gene delivery and stable transduction of nondividing cells by a lentiviral vector," *Science*, 272: 263-267 (1996).
Oh, C., et al., "Nucleophilic vinylic substitution of halocoumarins and halo-1,4-napthoquinones with morpholine," *J. Heterocyclic Chem.*, 1994, vol. 31, pp. 841-843.
*Remington 's Pharmaceutical Sciences*, 18th ed., Mack Pub. Co., Easton, PA (1990).
Roma, G., et al., "Synthesis, antiplatelet activity and comparative molecular field analysis of substituted 2-amino-4H pyrido[1,2- a]pyrimidin-4-ones, their congeners and isosteric analogues," *Bioorganic & Medicinal Chemistry*, 2000, vol. 8, pp. 751-768.

Roma, G., et al., "Pyran derivatives XX. 2-aminochromone benzo-fused derivatives with antiproliferative properties," *Il Farmaco*, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," *Clin. Cancer Res.*, 1997, vol. 3, 1149-1156.

Sarkaria, Jann N. et al., "Inhibition of ATM and ATR kinase activities by the radiosensitizing agent, caffeine," *Cancer Res.*, 59: 4375-4382 (1999).

Savitsky, Kinneret et al., "A single ataxia telangiectasia gene with a product similar to PI-3 kinase," *Science*, 268:1749-1753 (1995).

Schroth. W., et al., "2,4,6-Tris(dialkylarnino) pyrylium salts and related systems, synthesis and reaction behavior," *Tetrahedron Letters*, 1988, vol. 29, No. 37, pp. 4695-4698.

Schroth, W. et al., "2,4,6-Tris(dialkylamino) pyrylium salts and related systems, synthesis and reaction behavior," *Chemical Abstracts*, 110:135031.

Shiloh, Yosef, "ATM and ATR: networking cellular responses to DNA damage," *Curr. Opin. Genet. Dev.*, 11:71-77 (2001).

Sirzen, F. et al. Eur. J. Cancer (1999) 35:111-116.

Skehan. P.. et al., "New colorimetric cytotoxicity assay for anticancer-drug screening," *J. Natl. Cancer Inst.*, 1990, vol. 82, No. 13, pp. 1107-1112.

Smith, G. C. M., et al., "The DNA-dependent protein kinase," *Genes & Dev.*, 1999, vol. 13, pp. 916-934.

Snyder, et al., "Structure and reactions of malonyl-α-aminopyridine. I," *J. Am. Chem. Soc.*, 1952, vol. 74, pp. 4910-4914.

Ten Hoeve, et al., "Direct substitution of aromatic ethers by lithium amides. A new aromatic amination reaction," *J. Org. Chem.*, 1993, vol. 58, pp. 5101-5106.

Toker, Alex and Cantley, Lewis C., "Signalling through the lipid products of phosphoinositide-3-OH kinase," *Nature*, 387:673-676 (1997).

Veuger, S. J., et al., "Radiosensitization and DNA repair inhibition by the combined use of novel inhibitors of DNA-dependent protein kinase and poly (ADP-ribose) polymerase-1," *Cancer Research*, 2003, vol. 63, pp. 6008-6015.

Vlahos, C. J., et al., "A specific inhibitor of phosphatidylinositol 3-kinase, 2-(4-morpholinyl)-8-phenyl-4H-1-benzopyran-4-one (LY294002)," *J. Biol. Chem.*, 1994, vol. 269, No. 7, pp. 5241-5248.

Willmore et al., "A novel DNA-dependent protein kinase inhibitor, NU7026, potentiates the cytotoxicity of topoisomerase II poisons used in the treatment of leukemia", *Blood*, Jun. 15, 2004, vol. 103, No. 12, 4659-4665.

Wymann, M. T., et al., "Wortmannin inactivates phosphoinositide-3-kinase by covalent modification of Lys-802, a residue involved in the phosphate transfer reaction," *Mol. Cell Biol.*, 1996, vol. 16, No. 4, pp. 1722-1733.

Zakian, Virginia A., "ATM-related genes: What do they tell us about functions of the human gene?" *Cell*, 82:685-687 (1995).

United States Patent Office Action for U.S. Appl. No. 10/373,114 dated Aug. 31, 2004 (15 pages).

United States Patent Office Action for U.S. Appl. No. 10/373,114 dated Mar. 30, 2005 (5 pages).

United States Patent Office Action for U.S. Appl. No. 10/918,180 dated Jun. 6, 2007 (12 pages).

United States Patent Office Action for U.S. Appl. No. 10/918,180 dated Dec. 5, 2007 (6 pages).

United States Patent Office Action for U.S. Appl. No. 10/486,811 dated Sep. 19, 2005 (4 pages).

United States Patent Office Action for U.S. Appl. No. 10/486,811 dated Jan. 5, 2006 (4 pages).

United States Patent Office Action for U.S. Appl. No. 11/231,041 dated Jul. 19, 2007 (13 pages).

Bryn, S.R. et al., "Hydrates and solvates," in Solid-State Chemistry of Drugs, Second Edition (1999) 233-247.

United States Patent Office Action for U.S. Appl. No. 11/758,332 dated Mar. 25, 2009 (10 pages).

United States Patent Office Action for U.S. Appl. No. 11/403,606 dated Apr. 28, 2009 (9 pages).

United States Patent Office Action for U.S. Appl. No. 11/403,763 dated Apr. 29, 2009 (9 pages).

* cited by examiner

ATM INHIBITORS

CROSS-REFERENCE TO RELATED APPLICATIONS

This application claims the priority benefit of U.S. Provisional Patent Application Ser. No. 60/651,174 filed on Feb. 9, 2005. This provisional application is incorporated herein by reference.

The present invention relates to compounds which act as ATM inhibitors, their use and synthesis.

Human DNA is constantly under attack from reactive oxygen intermediates principally from by-products of oxidative metabolism. Reactive oxygen species are capable of producing DNA single-strand breaks and, where two of these are generated in close proximity, DNA double strand breaks (DSBs). In addition, single- and double-strand breaks can be induced when a DNA replication fork encounters a damaged template, and are generated by exogenous agents such as ionising radiation (IR) and certain anti-cancer drugs (e.g. bleomycin, etoposide, camptothecin). DSBs also occur as intermediates in site-specific V(D)J recombination, a process that is critical for the generation of a functional vertebrate immune system. If DNA DSBs are left unrepaired or are repaired inaccurately, mutations and/or chromosomal aberrations are induced, which in turn may lead to cell death. To combat the serious threats posed by DNA DSBs, eukaryotic cells have evolved several mechanisms to mediate their repair. Critical to the process of DNA repair is the slowing down of cellular proliferation to allow time for the cell to repair the damage. A key protein in the detection of DNA DSBs and in the signalling of this information to the cell cycle machinery is the kinase ATM (ataxia telangiectasia mutated) (Durocher and Jackson (2001) DNA-PK, ATM and ATR as sensors of DNA damage: variations on a theme? *Curr Opin Cell Biol.*, 13:225-31, Abraham (2001) Cell cycle checkpoint signaling through the ATM and ATR kinases. *Genes Dev.*, 15; 2177-96).

The ATM protein is a ~350 kDa polypeptide that is a member of the phosphatidylinositol (PI) 3-kinase family of proteins by virtue of a putative kinase domain in its carboxyl-terminal region (Savitsky et al (1995) A single ataxia telangiectasia gene with a product similar to PI-3 kinase. *Science*, 268:1749-53). Classical PI 3-kinases, such as PI 3-kinase itself, are involved in signal transduction and phosphorylate inositol lipids that act as intracellular second messengers (reviewed in Toker and Cantley (1997) Signalling through the lipid products of phosphoinositide-3-OH kinase, *Nature*, 387: 673-6). However, ATM bears most sequence similarity with a subset of the PI 3-kinase family that comprises proteins which, like ATM, are involved in cell cycle control and/or in the detection and signalling of DNA damage (Keith and Schreiber (1995) PIK-related kinases: DNA repair, recombination, and cell cycle checkpoints, *Science*, 270; 50-1, Zakian (1995) ATM-related genes: what do they tell us about functions of the human gene? *Cell*, 82; 685-7). Notably there is no evidence to date that any members of this subset of the PI 3-kinase family are able to phosphorylate lipids. However, all members of this family have been shown to possess serine/threonine kinase activity. ATM phosphorylates key proteins involved in a variety of cell-cycle checkpoint signalling pathways that are initiated in response to DNA DSBs production (see below). These downstream effector proteins include p53, Chk2, NBS1/nibrin, BRCA1 and Rad 17 (Abraham, 2001)

ATM is the product of the gene mutated in ataxia-telangiectasia (A-T) (Savitsky et al (1995)). A-T is a human autosomal recessive disorder present at an incidence of around 1 in 100,000 in the population. A-T is characterised by a number of debilitating symptoms, including progressive cerebellar degeneration, occulocutaneous telangiectasia, growth retardation, immune deficiencies, cancer predisposition and certain characteristics of premature ageing (Lavin and Shiloh (1997), The genetic defect in ataxia-telangiectasia. *Annu. Rev. Immunol.*, 15:177-202; Shiloh (2001), ATM and ATR: networking cellular responses to DNA damage, *Curr. Opin. Genet. Dev.*, 11:71-7). At the cellular level, A-T is characterised by a high degree of chromosomal instability, radio-resistant DNA synthesis, and hypersensitivity to ionizing radiation (IR) and radiomimetic drugs. In addition, A-T cells are defective in the radiation induced $G_1$-S, S, and $G_2$-M cell cycle checkpoints that are thought to arrest the cell cycle in response to DNA damage in order to allow repair of the genome prior to DNA replication or mitosis (Lavin and Shiloh, 1997). This may in part reflect the fact that A-T cells exhibit deficient or severely delayed induction of p53 in response to IR. Indeed, p53-mediated downstream events are also defective in A-T cells following IR exposure. ATM therefore acts upstream of p53 in an IR-induced DNA damage signalling pathway. A-T cells have also been shown to accumulate DNA double-strand breaks (dsbs) after ionizing radiation, suggesting a defect in dsb repair.

It is clear that ATM is a key regulator of the cellular response to DNA DSBs. Therefore the inhibition of this kinase through small molecules will sensitise cells to both ionising radiation and to chemotherapeutics that induce DNA DSBs either directly or indirectly. ATM inhibitors may thus be used as adjuncts in cancer radiotherapy and chemotherapy. To date the only reported inhibitors of ATM (caffeine and wortmannin; Sarkaria, et al., (1999) Inhibition of ATM and ATR kinase activities by the radiosensitizing agent, caffeine. *Cancer Res.*, 59:4375-82; Banin, et al., (1998) Enhanced phosphorylation of p53 by ATM in response to DNA damage. *Science*, 281:1674-1677) do cause radiosensitisation but it is unclear whether this mechanism of action is mediated through ATM inhibition as these small molecules are very non-specific in action as kinase inhibitors.

ATM function in response to ionising radiation induced DNA damage has been shown to be tissue specific. For example, while fibroblasts derived from Atm null mice are radiosensitive Atm null neurons are radioresistant through a lack of IR induced apoptosis (Herzog et al., (1998) Requirement for Atm in ionizing radiation-induced cell death in the developing central nervous system. *Science*, 280: 1089-91). Therefore, inhibitors of ATM have the potential to be radioprotective in specific cellular contexts.

ATM inhibitors may also prove useful in the treatment of retroviral mediated diseases. It has been demonstrated that ATM function is required to allow stable retroviral DNA transduction under certain conditions (Daniel et al. (2001) Wortmannin potentiates integrase-mediated killing of lymphocytes and reduces the efficiency of stable transduction by retroviruses. *Mol. Cell Biol.*, 21: 1164-72). Therefore ATM inhibitors have the potential to block retroviral DNA integration.

ATM is known to play a crucial role in controlling the length of telomeric chromosomal ends (Metcalfe et al. (1996) Accelerated telomere shortening in ataxia telangiectasia. *Nat Genet.*, 13:350-3). Telomeric ends in most normal cell types shorten at each cell division. Cells with excessively shortened telomeres are unable to divide. Inhibitors of ATM may therefore, have utility in preventing cancer progression by limiting the growth potential of cancerous or pre-cancerous cells. Furthermore, ATM does not appear to be part of the telomerase enzyme itself (Metcalfe et al. (1996)) Therefore it is likely that ATM inhibitors will work synergistically with antitelomerase drugs.

Cells derived from A-T patients or from mice null for ATM grow slower in culture than genetically matched ATM positive cells. Therefore an ATM inhibitor may have growth inhibitory/anti-proliferative properties in its own right. Therefore an ATM inhibitor may be used as a cytostatic agent in the treatment of cancer.

A-T patients display immuno-deficiencies, demonstrating that ATM is required for generation of a fully functional immune system. Inhibitors of ATM may, therefore, be used in modulating the immune system.

In summary ATM inhibitors have the potential to sensitise tumour cells to ionising radiation or DNA DSB inducing chemotherapeutics, to modulate telomere length control mechanisms, to block retroviral integration, modulate the immune system and to protect certain cell types from DNA damage induced apoptosis.

Some of the present inventors have previsouly described a broad class of compounds which exhibit inhibition of ATM, which are described in WO 03/070726, which is incorporated herein by reference.

The present inventors have now discovered further specific compounds which exhibit inhibition of ATM. Accordingly, the first aspect of the invention provides a compound of formula I:

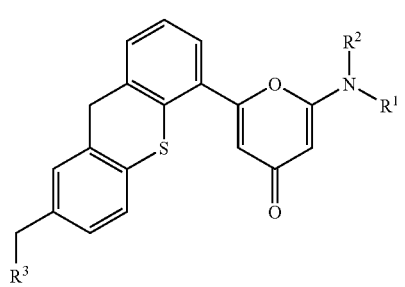

(I)

and isomers, salts, solvates, chemically protected forms, and prodrugs thereof, wherein:

$R^1$ and $R^2$ together form, along with the nitrogen atom to which they are attached, an optionally substituted nitrogen containing heterocyclic ring having from 4 to 8 ring atoms; and $R^3$ is selected from hydroxy and $-NR^{N1}R^{N2}$, where $R^{N1}$ and $R^{N2}$ are independently selected from hydrogen, optionally substituted $C_{1-7}$ alkyl groups, optionally substituted $C_{3-20}$ heterocyclyl groups and optionally substituted $C_{5-20}$ aryl groups, or together form, along with the nitrogen atom to which they are attached, an optionally substituted nitrogen containing heterocyclic ring having from 4 to 8 ring atoms.

A second aspect of the invention provides a composition comprising a compound of the first aspect and a pharmaceutically acceptable carrier or diluent.

A third aspect of the invention provides the use of a compound of the first aspect in a method of therapy.

A fourth aspect of the invention provides the use of a compound of the first aspect in the preparation of a medicament for inhibiting the activity of ATM.

A fifth aspect of the invention provides for the use of a compound of the first aspect of the invention in the preparation of a medicament for use as an adjunct in cancer therapy or for potentiating tumour cells for treatment with ionising radiation or chemotherapeutic agents.

A sixth aspect of the invention provides for the use of a compound of the first aspect of the invention in the preparation of a medicament for the treatment of retroviral mediated diseases or disease ameliorated by the inhibition of ATM, which include acquired immunodeficiency syndrome.

A further aspect of the invention provides an active compound as described herein for use in a method of treatment of the human or animal body, preferably in the form of a pharmaceutical composition.

Another aspect of the invention provides a method of inhibiting ATM in vitro or in vivo, comprising contacting a cell with an effective amount of an active compound as described herein.

Definitions $C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, $-CH=CH_2$), 2-propenyl (allyl, $-CH-CH=CH_2$), isopropenyl ($-C(CH_3)=CH_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$ heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g. fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heteroaryl groups which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

$C_{1-2}$ alkdioxylene: The term "$C_{1-2}$ alkdioxylene," as used herein, pertains to a bidentate moiety obtained by removing two hydrogen atoms from each of two different alcohol groups of a $C_{1-2}$ hydrocarbon diol compound having from 1 or 2 carbon atoms, i.e. $CH_2(OH)_2$ and $HO-CH_2-CH_2-OH$, to form $-O-CH_2-O-$ and $-O-CH_2-CH_2-O-$. This bidentate moiety may be the substituent group of a single atom or of two adjacent atoms.

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, $-O-C(=O)-$ in a ring), including, but not limited to, β-propiolactone, γ-butyrolactone, δ-valerolactone, and ε-caprolactone; and lactams (cyclic amides, $-NH-C(=O)-$ in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): $-C(=O)H$.

Acyl (keto): $-C(=O)R$, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, $-C(=O)CH_3$ (acetyl), $-C(=O)CH_2CH_3$ (propionyl), $-C(=O)C(CH_3)_3$ (butyryl), and $-C(=O)Ph$ (benzoyl, phenone).

Carboxy (carboxylic acid): $-COOH$.

Ester (carboxylate, carboxylic acid ester, oxycarbonyl): $-C(=O)OR$, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, $-C(=O)OCH_3$, $-C(=O)OCH_2CH_3$, $-C(=O)OC(CH_3)_3$, and $-C(=O)OPh$.

Acyloxy (reverse ester): $-OC(=O)R$, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, $-OC(=O)CH_3$ (acetoxy), $-OC(=O)CH_2CH_3$, $-OC(=O)C(CH_3)_3$, $-OC(=O)Ph$, and $-OC(=O)CH_2Ph$.

Amido (carbamoyl, carbamyl, aminocarbonyl, carboxamide): $-C(=O)NR^1R^2$, wherein $R^1$ and $R^2$ are independently amino substituents, as defined for amino groups. Examples of amido groups include, but are not limited to, $-C(=O)NH_2$, $-C(=O)NHCH_3$, $-C(=O)N(CH_3)_2$, $-C(=O)NHCH_2CH_3$, and $-C(=O)N(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): $-NR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, $-NHC(=O)CH_3$, $-NHC(=O)CH_2CH_3$, and $-NHC(=O)Ph$. $R^1$ and $R^2$ may together form a cyclic structure, as in, for example, succinimidyl, maleimidyl and phthalimidyl:

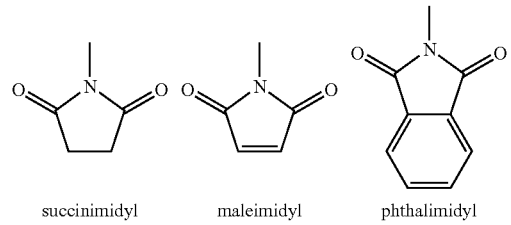

succinimidyl    maleimidyl    phthalimidyl

Thioamido (thiocarbamyl): $-C(=S)NR^1R^2$, wherein $R^1$ and $R^2$ are independently amino substituents, as defined for amino groups. Examples of amido groups include, but are not limited to, $-C(=S)NH_2$, $-C(=S)NHCH_3$, $-C(=S)N(CH_3)_2$, and $-C(=S)NHCH_2CH_3$.

Tetrazolyl: a five membered aromatic ring having four nitrogen atoms and one carbon atom,

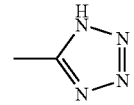

Amino: $-NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, $-NH_2$, $-NHCH_3$, $-NHC(CH_3)_2$, $-N(CH_3)_2$, $-N(CH_2CH_3)_2$, and $-NHPh$. Examples of cyclic amino groups include, but are not limited to, aziridino, azetidino, pyrrolidino, piperidino, piperazino, morpholino, and thiomorpholino.

Imino: =NR, wherein R is an imino substituent, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: $-C(=NR)NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is $-C(=NH)NH_2$.

Nitro: $-NO_2$.

Nitroso: $-NO$.

Azido: $-N_3$.

Cyano (nitrile, carbonitrile): $-CN$.

Isocyano: $-NC$.

Cyanato: $-OCN$.

Isocyanato: $-NCO$.

Thiocyano (thiocyanato): $-SCN$.

Isothiocyano (isothiocyanato): $-NCS$.

Sulfhydryl (thiol, mercapto): $-SH$.

Thioether (sulfide): $-SR$, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams—in these groups one of R$^1$ and R is a $C_{5-20}$ aryl group, preferably phenyl, whilst the other of R$^1$ and R is a bidentate group which links to the $C_{5-20}$ aryl group, such as a bidentate group derived from a $C_{1-7}$ alkyl group. Examples of such groups include, but are not limited to:

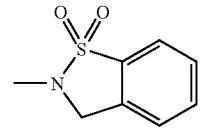

2,3-dihydro-benzo[d]isothiazole-1,1-dioxide-2-yl

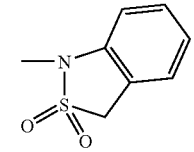

1,3-dihydro-benzo[c]isothiazole-2,2-dioxide-1-yl

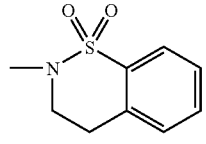

3,4-dihydro-2H-benzo[e][1,2]thiazine-1,1-dioxide-2-yl

Phosphoramidite: —OP(OR$^1$)—NR$^2_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$ alkoxy group), for example, cyclohexylmethoxy, a $C_{3-20}$ heterocyclyl group (also referred to as a $C_{5-20}$ aryl-$C_{1-7}$ alkoxy group), for example phthalimidoethoxy, or a $C_{5-20}$ aryl group (also referred to as a $C_{5-20}$aryl-$C_{1-7}$alkoxy group), for example, benzyloxy.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

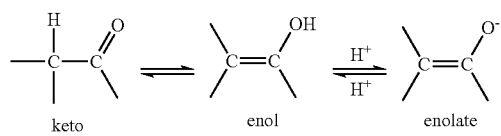

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", *J. Pharm. Sci.*, Vol. 66, pp. 1-19.

For example, if the compound is anionic, or has a functional group which may be anionic (e.g., —COOH may be —$COO^−$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(═O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include those wherein R is $C_{1-7}$ alkyl (e.g. —Me, —Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Further Preferences

The following preferences may be different for different aspects of the present invention, and may be combined together.

$R^1$ and $R^2$ $R^1$ and $R^2$ form, along with the nitrogen atom to which they are attached, a heterocyclic ring having from 4 to 8 atoms. This may form part of a $C_{4-20}$ heterocyclyl group defined above (except with a minimum of 4 ring atoms), which must contain at least one nitrogen ring atom. It is preferred that $R^1$ and $R^2$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrroe), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

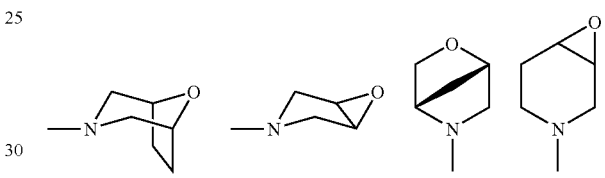

These are named 8-oxa-3-aza-bicyclo[3.2.1]oct-3-yl, 6-oxa-3-aza-bicyclo[3.1.0]hex-3-yl, 2-oxa-5-aza-bicyclo [2.2.1]hept-5-yl, and 7-oxa-3-aza-bicyclo[4.1.0]hept-3-yl, respectively.

$R^3$

If $R^3$ is —NR$^{N1}$R$^{N2}$, then R$^{N1}$ and R$^{N2}$ are preferably independently selected from hydrogen, optionally substituted $C_{1-7}$ alkyl groups or together form, along with the nitrogen atom to which they are attached, an optionally substituted heterocyclic ring having from 4 to 8 ring atoms.

If one of R$^{N1}$ and R$^{N2}$ is an optionally substituted $C_{1-7}$ alkyl group, the other is preferably also an optionally substituted $C_{1-7}$ alkyl group. The optionally substituted $C_{1-7}$ alkyl groups, are preferably an optionally substituted $C_{1-4}$ alkyl group (e.g. methyl, ethyl, n-propyl, n-butyl). The optional substituents are preferably selected from hydroxy, $C_{1-7}$ alkoxy (e.g. methoxy), amino (more preferably di-$C_{1-7}$ alkyl amino, e.g. dimethyl amino), $C_{3-20}$ heterocylyl (more preferably $C_{5-7}$ heterocylyl, e.g. derived from imidazolidinone) and $C_{5-20}$ aryl (more preferably $C_{5-7}$ aryl), and are more preferably selected from amino (more preferably di-$C_{1-7}$ alkyl amino, e.g. dimethyl amino), $C_{1-7}$ alkoxy (e.g. methoxy) and $C_{3-20}$ heterocylyl (more preferably $C_{5-7}$ heterocylyl, e.g. derived from imidazolidinone).

If R$^{N1}$ and R$^{N2}$ together form, along with the nitrogen atom to which they are attached, an optionally substituted heterocyclic ring having from 4 to 8 ring atoms, this ring preferably has 6 or 7 ring atoms, and is more preferably selected from piperidine, piperazine, homopiperazine and morpholino. Where the heterocyclic ring is piperazine or homopiperazine, the other nitrogen ring atom may be susbstituted by, for example, an optionally substituted $C_{1-7}$ alkyl group, an optionally substituted $C_{3-20}$ heterocyclyl group, an optionally substituted $C_{5-20}$ aryl group, an acyl group, an ester group or an amido group. Of these possible substituents, the optionally substituted $C_{1-7}$ alkyl group (e.g. methyl, propyl) and the optionally substituted $C_{5-20}$ aryl group (e.g. phenyl, pyrimidin-2-yl) are most preferred. Where the heterocylic ring is morpholino, these may be substituted, as discussed above. A preferred class of substituent is a $C_{1-7}$ alkyl group, more preferably methyl or ethyl, and most preferably methyl. A particular preferred embodiment has two methyl substituents, which may be, for example, both bound to the ring with the same orientation.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), acetyl (Ac), 1,3-bis(diphenylphosphino) propane (dppf).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis Routes

Compounds of the present invention where $R^3$ is an amine group may be synthesised by the coupling of 2-(7-bromomethyl-9H-thioxanthen-4-yl)-6-morpholin-4-yl-pyran-4-one (4) with an appropriate amine of formula $HNR^{N1}R^{N2}$, in the presence of a base, such as potassium carbonate.

Use of Compounds of the Invention

The present invention provides active compounds, specifically, active 2-aryl-6-amino-pyran-4-ones.

The term "active", as used herein, pertains to compounds which are capable of inhibiting ATM activity, and specifically includes both compounds with intrinsic activity (drugs) as well as prodrugs of such compounds, which prodrugs may themselves exhibit little or no intrinsic activity.

One assay which may be used in order to assess the ATM inhibition offered by a particular compound is described in the examples below.

The present invention further provides a method of inhibiting ATM in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit ATM activity as well as methods of inhibiting ATM activity comprising contacting a cell with an effective amount of an active compound, whether in vitro or in vivo.

The invention further provides active compounds for use in a method of treatment of the human or animal body. Such a method may comprise administering to such a subject a therapeutically-effective amount of an active compound, preferably in the form of a pharmaceutical composition.

The term "treatment" as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The term "adjunct" as used herein relates to the use of active compounds in conjunction with known therapeutic means. Such means include cytotoxic regimens of drugs and/or ionising radiation as used in the treatment of different cancer types. In particular, the active compounds are known to potentiate the actions of a number of cancer chemotherapy treatments, which include, but are not limited to, the topoisomerase class of poisons and any chemotherapeutic that will induce a DNA double strand break used in treating cancer. Topoisomerase I inhibitors that may be used in combination with compounds of the invention include the camptothecin compounds, e.g. topotecan (Hycamtin), irinotecan (CPT11-Camptosar), rubitecan and exatecan. Dual Topoisomerase I and II inhibitors that may be used in combination with compounds of the invention include benzophenainse, XR 11576/MLN 576 and benzopyridoindoles. Topoisomerase II inhibitors that may be used in combination with compounds of the invention include the intercalators and DNA binders Doxorubicin, Danorubicin, and other rubicins, the acridines (Amsacrine, m-AMSA), plus Mitoxantrone and AQ4. Non-intercalators which are topoisomerase II inhibitors include Etopside and Teniposide (epipodophyllotoxins).

It has been previously disclosed (WO 03/070726) that ATM inhibitory compounds of similar structure to those of the present invention can efficiently repress retroviral vector transduction in one-step, cell based integration assays (termed LUCIA) and inhibit HIV-1 infection in 4-day replication assays at sub-micromolar concentrations. Further, in contrast to the observations of Daniel et al., where it was concluded that the effect of ATM on retroviral integration would only be seen in a DNA-PK-deficient background, this effect works in the presence of functional DNA-PK activity.

Initial linkage of linear retroviral DNA with host cell chromosomal DNA is catalysed by viral integrase (IN) and results in short staggered DNA strand breaks in the host cell DNA at the site of attachment (Brown, P.O. (1990) Integration of retroviral DNA. *Curr Top Microbiol Immunol*, 157, 19-48). These gapped DNA intermediates are shown to be sensed as sites of DNA damage by the host cell and repaired by the ATM pathway to complete the process of integration and allow productive infection to occur. Compounds of the invention would be able to prevent the repair of gapped DNA intermediates by the ATM pathway and thus prevent complete integration of retroviral DNA into the host genome.

As described above, the invention provides a compound as defined in the first aspect of the invention for use in the treatment of retroviral infection and the use of such a compound in the manufacture of a medicament for use in the treatment of retroviral infection.

Also provided by the invention is a method of treatment of a retroviral infection comprising administering a compound as defined in the first aspect of the invention to an individual in need thereof.

Retroviral mediated diseases which may be treated as described above include HIV infection and acquired immunodeficiency syndrome (AIDS) and Human T-cell Leukaemia virus (HTLV) infection and its associated diseases adult T-cell leukaemia/lymphoma (ATLL) and tropical spastic paraparesis/HTLV-1 associated myelopathy (TSP/HAM).

Compounds of the invention may be used in combination with other retroviral therapies to suppress virus replication, for example in a 'highly active anti-retroviral therapy' or HAART treatment.

The invention provides a pharmaceutical composition comprising a compound as described herein and one or more other anti-retroviral agents.

The invention also provides a composition comprising a compound as defined in the first to ninth aspects of the invention and one or more other anti-retroviral agents for treatment of a retroviral infection and the use of such a composition in the manufacture of a medicament for use in the treatment of a retroviral infection.

Suitable anti-retroviral agents which inhibit retroviral replication, for example retroviral protease inhibitors (PI) such as Sequinavir, Indinavir, Ritonavir and Nelfinavir, nucleoside retroviral reverse transcriptase inhibitors such as 3'-azido-3'deoxythymidine (AZT; Zidovudine), 2',3'-Dideoxycytosine (ddC; Zalcitabine), 2',3'-Dideoxyinosine (ddI; Didanosine) and 3TC; (Lamivudine), and non-nucleoside retroviral reverse transcriptase inhibitors such as Nevirapine, Delavirdine and Efavirenz.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

A) Chemical Examples

General Experimental Methods

Compounds were purified on Gilson LC units.

Mobile phase A—0.1% aqueous TFA, Mobile phase B—Acetonitrile, Flow rate 6 ml/min., Gradient—typically starting at 90% A/10% B for one minute, rising to 97% B after 15 minutes, holding there for 2 minutes, then back to the starting conditions. Column: Jones Chromatography Genesis 4μ C18 column, 10 mm×250 mm. Peak acquisition based on UV detection at 254 nm.

Mass Specs were recorded on a Finnegan LCQ instrument in positive ion mode.

Example 1

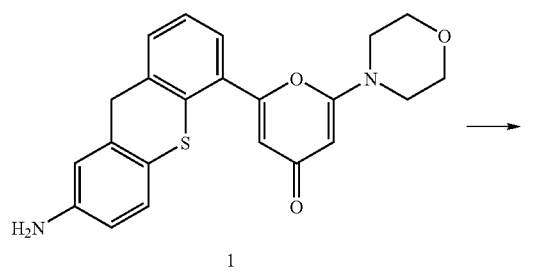

1

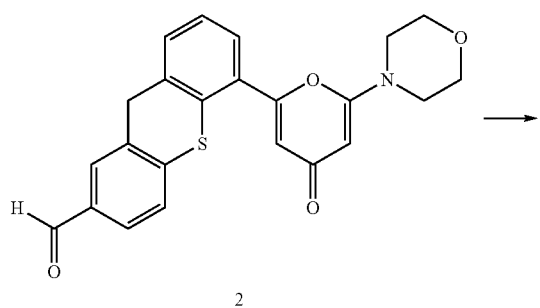

2

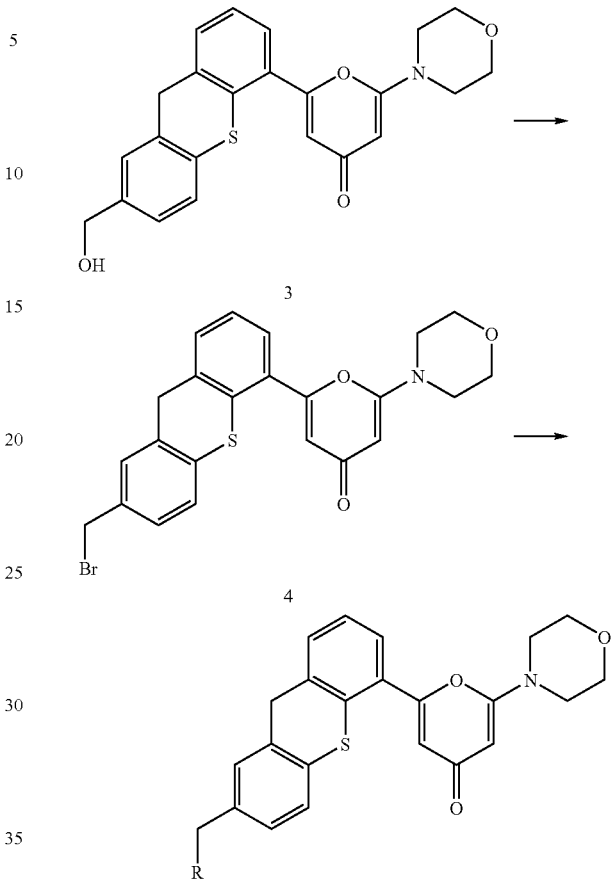

2-(7-Amino-9H-thioxanthen-4-yl)-6-morpholin-4-yl-pyran-4-one (1) was synthesised as described in WO 03/070726 (compound 20).

5-(6-Morpholin-4-yl-4-oxo-4H-pyran-2-yl)-9H-thioxanthene-2-carboxaldehyde (2)

To a suspension of 2-(7-amino-9H-thioxanthen-4-yl)-6-morpholin-4-yl-pyran-4-one (1)(0.50 g, 1.27 mmol) in ethanol (4 mL) at room temperature was added tetrafluorboric acid (supplied as 54 wt % in diethyl ether, 0.35 mL, 2.54 mmol). The solution was then cooled to 0° C., when t-butyl nitrite (750 μL, 6.33 mmol) was added. After 1 hr, the reaction was diluted with diethyl ether (10 mL), and after 20 mins the precipitate was filtered and washed with diethyl ether. The orange coloured salt was then dissolved in MeCN:Et$_2$O (1:1) (15 mL), when triisopropylsilane (222 mg, 1.40 mmol) and Pd(OAc)$_2$ (5.47 g, 24.37 mmol) were added successively. A CO pressure of 10 atm was then applied for 10 minutes, after which the reaction was filtered. The organic layer was washed with saturated NaHCO$_3$ then brine, dried over MgSO$_4$, filtered and concentrated in vacuo. The resulting yellow/orange solid was dried under vacuum at 50° C. to give the crude title compound (0.392 g, 75%, 2 steps) which was used without any further purification. m/z (LC-MS, ESP), RT=3.40 min, (M$^+$+1)=406.3

2-(7-Hydroxymethyl-9H-thioxanthen-4-yl)-6-morpholin-4-yl-pyran-4-one (3)

To a suspension of 5-(6-Morpholin-4-yl-4-oxo-4H-pyran-2-yl)-9H-thioxanthene-2-carbaldehyde (2)(0.392 g, 0.97 mmol) in ethanol (7 mL) at room temperature was added sodium cyanoborohydride (121 mg, 1.93 mmol), followed by the addition of acetic acid (1 mL). After 5 hours, a second addition of acetic acid (1 mL) was made. After a further 12 hours, the excess borohydride was quenched with acetone. After evaporation in vacuo, saturated NaHCO$_3$ was added, followed by extraction into dichloromethane. The combined organic layers were dried over MgSO$_4$, filtered and concentrated in vacuo. The brown coloured solid was dried under vacuum at 50° C. to give the crude title compound (0.332 g, 84%) which was used without any further purification. m/z (LC-MS, ESP), RT=3.09 min, (M$^+$+1)=408.3

2-(7-Bromomethyl-9H-thioxanthen-4-yl)-6-morpholin-4-yl-pyran-4-one (4)

A solution of 2-(7-Hydroxymethyl-9H-thioxanthen-4-yl)-6-morpholin-4-yl-pyran-4-one (3)(240 mg, 0.59 mmol) in chloroform (10 mL) was saturated with hydrogen bromide by bubbling hydrogen bromide gas through the reaction mixture until the solution became cloudy. After 18 hours, hydrogen bromide gas was again bubbled through the reaction mixture. The reaction mixture was washed with saturated NaHCO$_3$ and water. The organic layer was dried over MgSO$_4$, filtered and concentrated in vacuo. The brown coloured solid was dried under vacuum at 50° C. to give the crude title compound (assumed 100%) which was used without any further purification. m/z (LC-MS, ESP): 470.2 [M+H]$^+$ (1:1, bromine isotope ratio present), R/T=3.86 mins

2-(7-Aminomethyl-9H-thioxanthen-4-yl)-6-morpholin-4-yl-pyran-4-one N-amide derivatives To a small test tube was added 2-(7-Bromomethyl-9H-thioxanthen-4-yl)-6-morpholin-4-yl-pyran-4-one (4)(23 mg, 0.05 mmol), dry dimethylacetamide (1 mL), potassium carbonate (137 mg, 0.10 mmol) and the desired amines (0.10 mmol). After overnight stirring at room temperature, the reaction mixtures were purified by preparative HPLC to provide the desired products, as set out below:

| Compound | R | Purity (%) | Retention Time (mins) | M$^+$ + 1 |
|---|---|---|---|---|
| 5 | cis-2,6-dimethylmorpholin-4-yl | 94 | 3.84 | 505 |
| 6 | N,N,N'-trimethylethylenediamine-N'-yl | 85 | 3.49 | 492 |
| 7 | 4-(2-methoxyethyl)piperazin-1-yl | 84 | 3.75 | 534 |
| 8 | bis(2-methoxyethyl)amino | 97 | 3.92 | 523 |
| 9 | 4-methylpiperazin-1-yl | 96 | 3.69 | 490 |
| 10 | 4-isopropylpiperazin-1-yl | 98 | 3.76 | 518 |
| 11 | 4-(pyrimidin-2-yl)piperazin-1-yl | 96 | 3.88 | 554 |
| 12 | 1,4-diazepan-1-yl | 88 | 3.43 | 490 |
| 13 | diethylamino | 98 | 3.81 | 463 |
| 14 | 2-(2-oxoimidazolidin-1-yl)ethylamino | 87 | 3.69 | 519 |
| 15 | morpholin-4-yl | 94 | 3.91 | 477 |

B) Biological Examples

Materials and Methods

In Vitro ATM Inhibition Assays

In order to assess the inhibitory action of the compounds against ATM in vitro, the following assay was used to determine IC$_{50}$ values.

ATM protein was immunoprecipitated from HeLa cell nuclear extract using rabbit polyclonal anti-sera raised to the C-terminal ~500 amino-acid residues of the human ATM protein. The immunoprecipitation was performed according to the methodology described by Banin, S. et al. (1998). 10 μl of immunoprecipitated ATM in Buffer C (50 mM Hepes, pH 7.4, 6 mM MgCl$_2$, 150 mM NaCl, 0.1 mM sodium orthovanadate, 4 mM MnCl$_2$, 0.1 mM dithiothreitol, 10% glycerol) was added to 32.5 µl of buffer C containing 1 µg of the ATM substrate GSTp53N66 in a V-bottomed 96 well polypropylene plate. The GSTp53N66 substrate is the amino terminal 66 amino acid residues of human wild type p53 fused to glutathione S-transferase. ATM phosphorylates p53 on the residue serine 15 (Banin, S. et al. (1998)). Varying concentrations of inhibitor were then added. All compounds were diluted in DMSO to give a final assay concentration of between 100 µM and 0.1 nM, with DMSO being at a final concentration of 1%. After 10 minutes of incubation at 37° C., the reactions were initiated by the addition of 5 µl of 500 µM Na-ATP. After 1 hour with shaking at 37° C., 150 µl of phosphate buffered saline (PBS) was added to the reaction and the plate centrifuged at 1500 rpm for 10 minutes. 5 µl of the reaction was then transferred to a 96 well opaque white plate containing 45 µl of PBS to allow the GSTp53N66 substrate to bind to the plate wells. The plate was covered and incubated at room temperature for 1 hour with shaking before discarding the contents. The plate wells were washed twice by the addition of PBS prior to the addition of 3% (w/v) bovine serum albumin (BSA) in PBS. The plate was incubated at room temperature for 1 hour with shaking before discarding the contents and washing twice with PBS. To the wells, 50 µl of a 1:10,000 dilution of primary phosphoserine-15 antibody (Cell Signaling Technology, #9284L) in 3% BSA/PBS was added to detect the phosphorylation event on the serine 15 residue of p53 elicited by the ATM kinase. After 1 hour of incubation at room temperature with shaking, the wells were washed four times with PBS prior to the addition of an anti-rabbit HRP conjugated secondary antibody (Pierce, 31462) with shaking for 1 hour at room temperature. The wells were then washed four times with PBS before the addition of chemiluminescence reagent (NEN Renaissance, NEL105). The plate was then shaken briefly, covered with a transparent plate seal and transferred to a TopCount NXT for chemiluminescent counting. Counts per second, following a one second counting time, were recorded for each reaction.

The enzyme activity for each compound is then calculated using the following equation:

$$\% \text{ Inhibition} = 100 - \left( \frac{(cpm \text{ of unknown} - \text{mean negative } cpm) \times 100}{(\text{mean positive } cpm - \text{mean negative } cpm)} \right)$$

Results

In Vitro ATM Assays

Compounds were assayed for ATM inhibition activity using the method described above. The results are detailed below as $IC_{50}$ values (the concentration at which 50% of the enzyme activity is inhibited). These are determined over a range of different concentrations, normally from 100 µM down to 0.1 nM. Such $IC_{50}$ values are used as comparative values to identify increased compound potencies.

All the compounds tested had $IC_{50}$ values of less than 200 nM.

The invention claimed is:

1. A compound of formula (I)

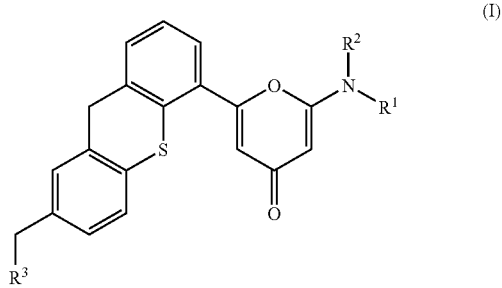

and geometric isomers, optical isomers, enantiomers, diastereomers, epimeric isomers, stereoisomers, tautomers, conformational isomers, anomeric isomers, compounds with one or more isotopic substitutions, salts, chemically protected forms, and prodrugs thereof, wherein: $R^1$ and $R^2$ together form, along with the nitrogen atom to which they are attached, an optionally substituted nitrogen containing heterocyclic ring having from 4 to 8 ring atoms; and $R^3$ is —$NR^{N1}R^{N2}$, wherein $R^{N1}$ and $R^{N2}$ are independently optionally substituted $C_{1-7}$ alkyl groups, or $R^{N1}$ and $R^{N2}$ together form, along with the nitrogen atom to which they are attached, an optionally substituted heterocyclic ring having 6 or 7 ring atoms.

2. A compound according to claim 1, wherein $R^{N1}$ and $R^{N2}$ together form, along with the nitrogen atom to which they are attached, an optionally substituted heterocyclic ring having 6 or 7 ring atoms.

3. A compound according to claim 2, wherein $R^{N1}$ and $R^{N2}$ together form, along with the nitrogen atom to which they are attached, a ring selected from piperidine, piperazine, homopiperazine and morpholino.

* * * * *